US010649308B2

(12) United States Patent
Zou et al.

(10) Patent No.: US 10,649,308 B2
(45) Date of Patent: May 12, 2020

(54) COHERENT PHOTON ANALOG-TO-DIGITAL CONVERSION DEVICE

(71) Applicant: Shanghai Jiao Tong University, Shanghai (CN)

(72) Inventors: Weiwen Zou, Shanghai (CN); Guang Yang, Shanghai (CN); Lei Yu, Shanghai (CN); Na Qian, Shanghai (CN); Jianping Chen, Shanghai (CN)

(73) Assignee: Shanghai Jiao Tong Technology, Shanghai (CN)

( * ) Notice: Subject to any disclaimer, the term of this patent is extended or adjusted under 35 U.S.C. 154(b) by 0 days.

(21) Appl. No.: 16/513,346

(22) Filed: Jul. 16, 2019

(65) Prior Publication Data
US 2019/0339588 A1 Nov. 7, 2019

Related U.S. Application Data

(63) Continuation of application No. PCT/CN2017/080975, filed on Apr. 18, 2017.

(30) Foreign Application Priority Data

Mar. 29, 2017 (CN) .......................... 2017 1 0198217

(51) Int. Cl.
H03M 1/12 (2006.01)
G02F 7/00 (2006.01)
(Continued)

(52) U.S. Cl.
CPC .............. G02F 7/00 (2013.01); H01S 3/1068 (2013.01); H04L 7/0331 (2013.01);
(Continued)

(58) Field of Classification Search
CPC ..... H03M 1/12; H03M 1/1071; A61B 5/1455; A61B 5/14551
(Continued)

(56) References Cited

U.S. PATENT DOCUMENTS

2002/0163454 A1 11/2002 Yap et al.
2011/0118572 A1* 5/2011 Bechtel ................ A61B 5/0059
600/322

FOREIGN PATENT DOCUMENTS

CN 106230516 A 12/2016
CN 106444215 A 2/2017
(Continued)

OTHER PUBLICATIONS

Yang, Guang et al., "Compensation of multi-channel mismatches in high-speed high-resolution photonic analog-to-digital converter," Optics Express, vol. 24, No. 21, 24061 (Oct. 7, 2016).
(Continued)

Primary Examiner — Joseph J Lauture
(74) Attorney, Agent, or Firm — Mei & Mark LLP; Manni Li

(57) ABSTRACT

A coherent photon analog-to-digital conversion device comprising an optical clock oscillation source, a sampled signal source, a photon sampling gate, a photoelectric detection module, an electrical sampling module, a phase detection module, a loop filter, and signal feedback links. By adjusting the optical clock oscillating source or the sampled signal source, the invention makes the two highly coherent, thereby reducing the clock jitter and greatly improving the sampling precision. It is very important for improving the performance of microwave photon systems that require high time accuracy and high sampling accuracy, such as microwave photon radar and optical communication systems.

9 Claims, 4 Drawing Sheets

(51) Int. Cl.
  *H01S 3/106*   (2006.01)
  *H04L 7/033*   (2006.01)
  *G02F 1/35*   (2006.01)
  *A61B 5/1455*   (2006.01)
  *H03M 1/10*   (2006.01)

(52) U.S. Cl.
  CPC ......... *A61B 5/1455* (2013.01); *A61B 5/14551* (2013.01); *G02F 1/3526* (2013.01); *H03M 1/1071* (2013.01); *H03M 1/12* (2013.01)

(58) Field of Classification Search
  USPC ........ 341/155, 120; 600/322, 323, 328, 473, 600/476
  See application file for complete search history.

(56) References Cited

FOREIGN PATENT DOCUMENTS

| | | |
|---|---|---|
| CN | 106444216 A | 2/2017 |
| CN | 106452432 A | 2/2017 |

OTHER PUBLICATIONS

Jungwon Kim et al., "Drift-free femtosecond timing synchronization of remote optical and microwave sources," Nature Photonics, vol. 2, pp. 733-736 (Dec. 2008).

\* cited by examiner

COHERENT PHOTON ANALOG-TO-DIGITAL CONVERSION DEVICE

CROSS-REFERENCE TO RELATED APPLICATIONS

The subject application is a continuation of PCT/CN2017/080975 filed on Apr. 18, 2017, which in turn claims priority on Chinese Application No. CN201710198217.1 filed on Mar. 29, 2017 in China. The contents and subject matter of the PCT international application and the Chinese priority application are incorporated herein by reference.

FIELD OF TECHNOLOGY

The invention relates to optical information processing technology, particularly, a coherent photon analog-to-digital conversion device, which realizes high-precision acquisition of radio frequency signals or optical signals.

BACKGROUND ART

Photon sampling technology has played an important role in high-speed signal processing and conversion, high-resolution measuring equipment, and optical signal quality testing. At present, high-performance photon sampling technology is at the stage of rapid development. The two major developing trends are ultra-high sampling rate and ultra-high precision. Considering from the aspect of the high sampling rate, the WDM/TDM scheme of the optical clock of the mode-locked laser can realize the multiplication of sampling rate, improve the sampling rate, and has the characteristics of strong stability, low clock jitter, and low electric processing quantization rate, so it is regarded as the best scheme of photon analog-to-digital conversion. In the current reported studies, the passive mode-locked laser is generally selected as the seed light source due to its low noise. However, the passive mode-locked laser has a low repetition frequency, and the acquisition of the high-rate photon sampling clock requires more multiplexing channels, which often leads to large structure and more stringent requirement for the precision of channel matching. With the development of the active mode-locked laser technology, the noise of active mode-locked lasers has been able to be reduced to a lower level. Using an active mode-locked laser with low jitter as the light source, based on its advantage of high repetition frequency, a photon sampling clock with high quality and ultra-high speed can be obtained only through a few multiplexing channels, which is of great significance for improving the performance index of the optical to digital conversion system and optimizing the system scheme.

However, clock jitter is a significant factor that limits the accuracy of photon sampling. Therefore, when improving the performance of a photon sampling system, the problem it faces is how to reduce the clock jitter between the photon sampling clock and the sampled signal source. In order to eliminate the relative clock jitter between the photon sampling clock and the signal to be sampled, it is necessary to improve the coherence between the two. One of these techniques is based on the same highly stable light source to simultaneously generate a coherent signal and a sampling clock, and the PADC resolution limit at this time will depend on the clock jitter of the light source itself. However, in practical applications, the broader case is that both the signal to be sampled and the sampling clock are generated from different signal sources.

Therefore, there is a need to realize high performance coherence between different electron and photon signal sources. Phase-locked technology is an effective means to realize coherent. By locking the frequency and phase of the controlled signal and the reference signal, their frequency and phase remain fixed, which reduces the clock jitter and improves the stability of the system.

Coherent phase-locked technology mainly includes the following. The first one is a photoelectric phase-discriminated and phase-locked technology that is based on optical nonlinear effects (J. Kim et al., "Drift-free femtosecond timing synchronization of remote optical and microwave sources," Nature Photonics, 2008, 2: 733-736), where a variety of nonlinear optical crystals have been developed, and the crystal with second-harmonic generation effect (SHG) and sum frequency effect has great application prospects in optical phase detection. In a long-distance optical fiber transmission system, a photon phase discriminator composed of a crystal having a second-harmonic generation effect is used to measure the phase shift between the signals at the sending and receiving ends and feed it back. The photon phase discriminator and the photoelectric locked system based on the frequency crystal (See J. Kim et al., Nature Photonics, 2008, 2: 733-736) adopt an all-fiber structure, the stability of the system is high, and the phase discriminator adopts a balanced structure, which effectively eliminates the noise introduced by the channel imbalance. However, the phase-locked technology based on nonlinear crystal has obvious shortcomings. The system structure is complex and difficult to integrate. At the same time, the performance and stability of the nonlinear crystal are greatly affected by the environment, which limits the applicable environment of the system.

Another photoelectric phase-discriminated and phase-locked technology is based on the microwave photonic device. The most direct method of the technology is to convert the optical signal into an electrical signal, and then use the electrical phase-locked loop for phase discrimination and phase locking, that is, only add PD to the front stage of the RF mixer, then it is a photoelectric phase discriminator based on the RF mixer. The technology is suitable for the locking of optical signals and electrical signals and the locking between optical signals and has the advantages of simple principle and low implementation cost. However, due to the bandwidth limitation of the RF mixer, it cannot be applied to systems with high frequency or high bandwidth, and the system noise is large.

However, although the existing photon sampling techniques and coherent locking techniques have been widely studied, the sampling methods combining the two have not been studied. Therefore, we propose a coherent photon analog-to-digital conversion method.

SUMMARY OF THE INVENTION

The object of the present invention is to provide a coherent photon analog-to-digital conversion device aiming at curing the deficiencies of the existing technology. The device adjusts the optical clock oscillation source or the sampled signal source to make them highly coherent, thereby reducing clock jitter and greatly improving sampling accuracy.

The technical solution of present invention is as follows:

A coherent photon analog-to-digital conversion device, comprising an optical clock oscillation source, a photon sampling gate, a sampled signal source, a photoelectric detection module, an electrical sampling module, a phase detection module, a loop filter, a first signal feedback link, and a second signal feedback link.

In the device of the present invention, the first output of the optical clock oscillation source is connected with the first input of the photon sampling gate; the output of the sampled signal source is connected with the second input of the photon sampling gate; the output of the photon sampling gate is connected with the input of the photoelectric detection module; the output of the photoelectric detection module is divided into two parts: one is connected with the electrical sampling module, and the other is connected with the first input of the phase detection module; the second output of the optical clock oscillation source is connected with the second input of the phase detection module; the output of the phase detection module is connected with the input of the loop filter; when the output of the loop filter is connected with the input of the optical clock oscillation source via the first signal feedback link, the locking of the optical clock oscillator source is realized; when the output of the loop filter is connected with the input of the sampled signal source via the second signal feedback link, the locking of the sampled signal source is realized.

In the present invention, the optical clock oscillation source is a passive mode-locked laser, an active mode-locked laser or a modulation frequency comb.

In the present invention, the sampled signal source is a voltage controlled oscillator, a frequency synthesizer source, a passive mode-locked laser, an active mode-locked laser or a modulated frequency comb.

In the present invention, the photon sampling gate is a lithium niobate electro-optic modulator, a polymer electro-optic modulator, a silicon-based integrated electro-optic modulator, a spatial light modulator, a photonic crystal fiber or a highly nonlinear fiber.

In the present invention, the photoelectric detection module is a PIN or an APD.

In the present invention, the electrical sampling module is an oscilloscope or an information processing card.

In the present invention, the phase detection module is a RF mixer, which is used for generating a desired mixing signal.

In the present invention, the loop filter is an RF low pass filter.

In the present invention, the first signal feedback link and the second signal feedback link are power amplifiers or PID servers.

Based on the above technical features, the present invention is advantageous in that:

1. The electro-optical photon sampling gate or all-optical photon sampling gate is adopted to realize coherent photon analog-to-digital conversion and complete signal sampling and coherent locking at the same time, which completes coherent locking of electro-optical oscillation source and optical-optical oscillation source, thus realizing the acquisition of electrical and optical signals.

2. The phase error information of the sampled signal and the sampling clock source reference output is fed back to the optical clock oscillation source or the sampled signal source to improve the coherence between the optical sampling clock and the sampled signal source, which can break through the theoretical limit of clock jitter and improve the sampling precision of the system.

BRIEF DESCRIPTION OF THE DRAWINGS

FIGS. 3A and 3B represent Amplitude (dB).

DETAILED DESCRIPTIONS OF THE INVENTION AND EMBODIMENTS

In combination with figures and embodiments hereunder, the present invention will be described in detail, but the scope of the present invention is not limited to the embodiments described below.

Figure 1:
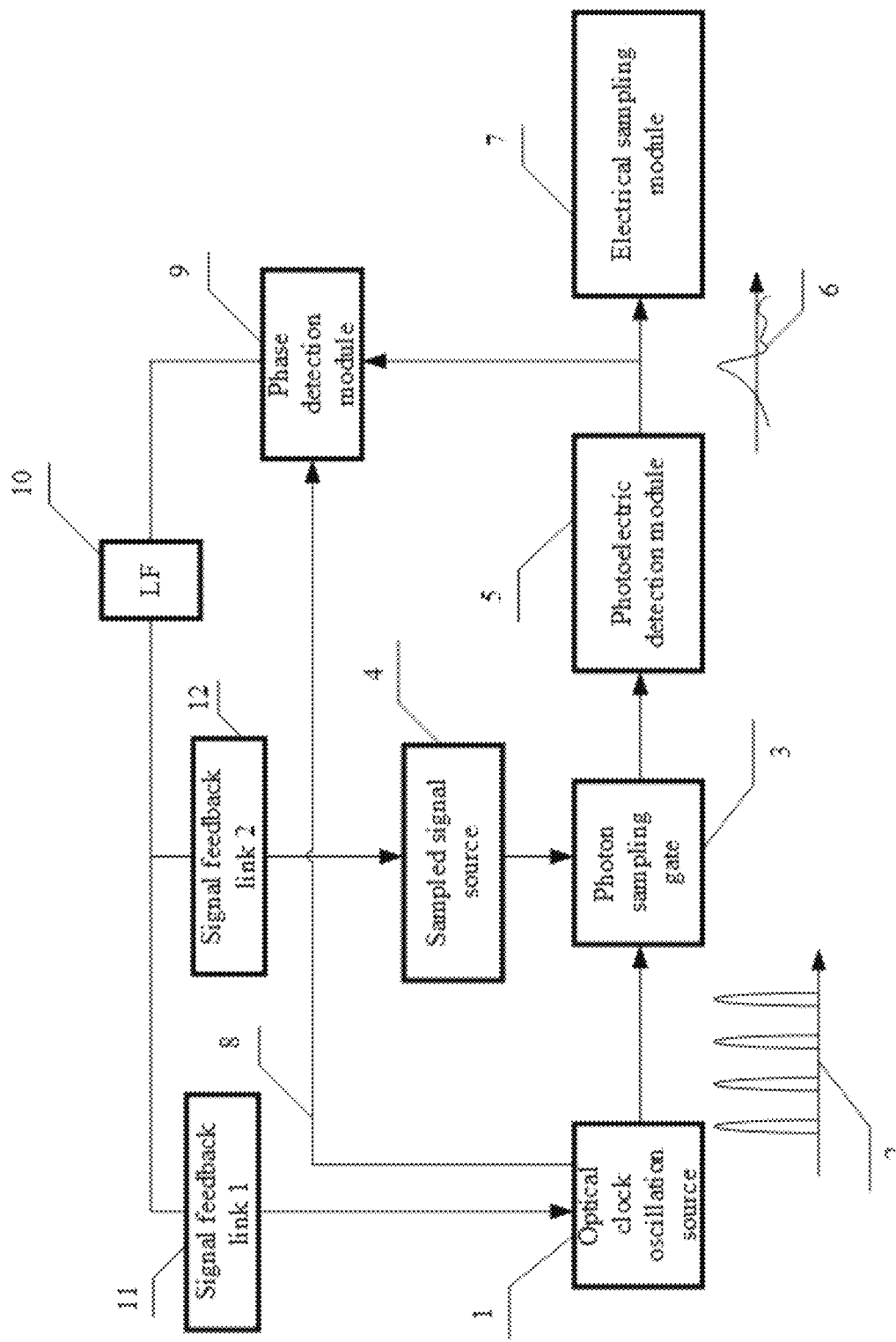
FIG. 1 is a block diagram showing one embodiment of the coherent photon analog-to-digital conversion device of present invention.
Figure 2:
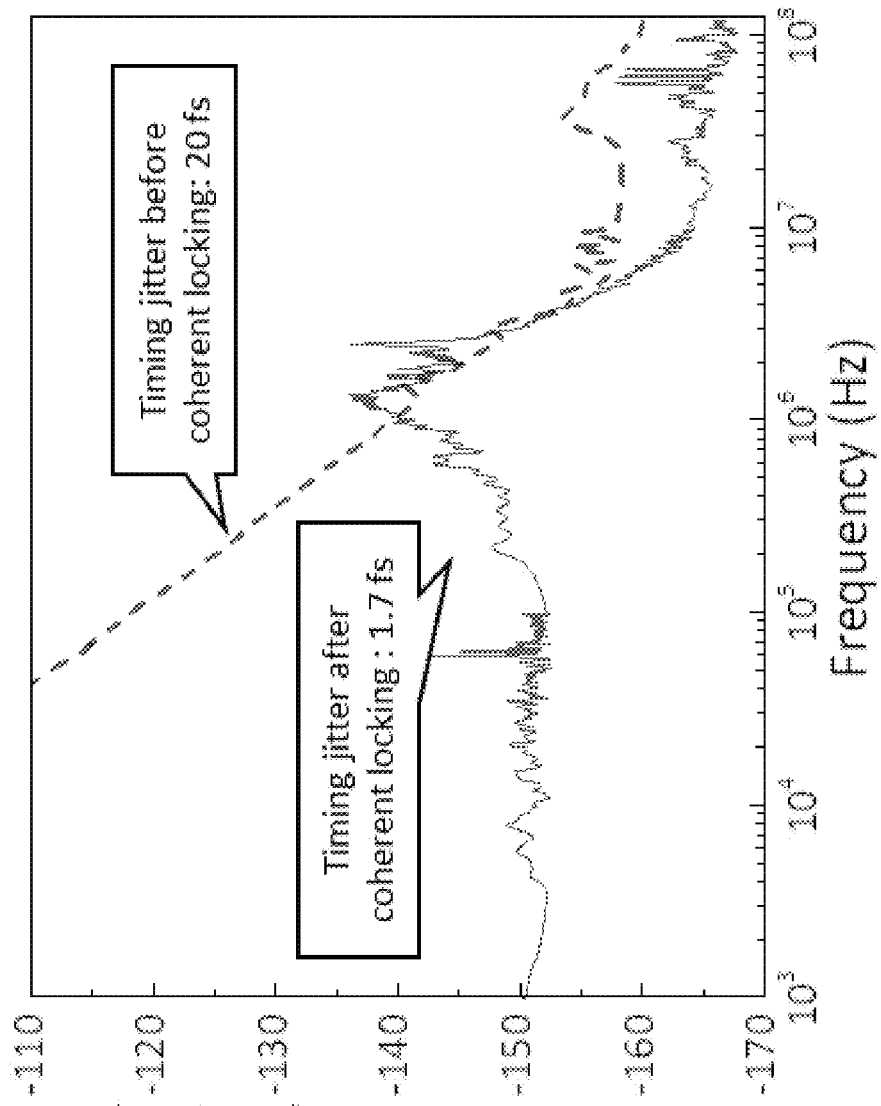
FIG. 2 shows the result of clock jitter test before and after coherent locking of the system in the present invention, where the vertical axis represents SSB phase noise (dBc/Hz).

As shown in FIG. 1, the coherent photon analog-to-digital conversion device of the present invention comprises an optical clock oscillation source 1, a photon sampling gate 3, a sampled signal source 4, a photoelectric detection module 5, an electrical sampling module 7, a phase detection module 9, a loop filter 10, a first signal feedback link 11, and a second signal feedback link 12.

As shown in FIG. 1, the first output of the optical clock oscillation source 1 is connected with the first input of the photon sampling gate 3; the output of the sampled signal source 4 is connected with the second input of the photon sampling gate 3; the output of the photon sampling gate 3 is connected with the input of the photoelectric detection module 5. The output of the photoelectric detection module 5 is divided into two parts, where one part is connected with the electrical sampling module 7, and the other part is connected with the first input of the phase detection module 9. The second output of the optical clock oscillation source 1 is connected with the second input of the phase detection module 9; the output of the phase detection module 9 is connected with the input of the loop filter 10. When the output of the loop filter 10 is connected with the input of the optical clock oscillation source 1 via the first signal feedback link 11, the locking of the optical clock oscillator source is realized. When the output of the loop filter 10 is connected with the input of the sampled signal source 4 via the second signal feedback link 12, the locking of the sampled signal source is realized.

In the present invention, optical clock oscillation source 1 is used to generate the optical sampling clock signal 2, the photon sampling gate 3 loads the electrical signal or optical signal to be sampled generated by the sampled signal source 4 to the optical clock signal 2, and the obtained result is converted into an electrical signal 6 by the photoelectric detection module 5. The electrical signal after conversion is divided into two parts: one part passes through the electrical sampling module 7 to realize the collection of the sampled signal; on the other hand, optical clock oscillation source 1 can generate a synchronized reference output signal 8 by photoelectric conversion, the reference output signal 8 and the other part of the electrical signal 6 are phase-detected by the phase detection module 9, and the obtained mixing signal filters out high frequency components by loop filter 10. Coherent locking with optical clock oscillation source 1 is achieved by the first signal feedback link 11, or coherent locking with sampled signal source 4 is achieved by the second signal feedback link 12, thereby achieving coherent sampling.

Figure 3B:
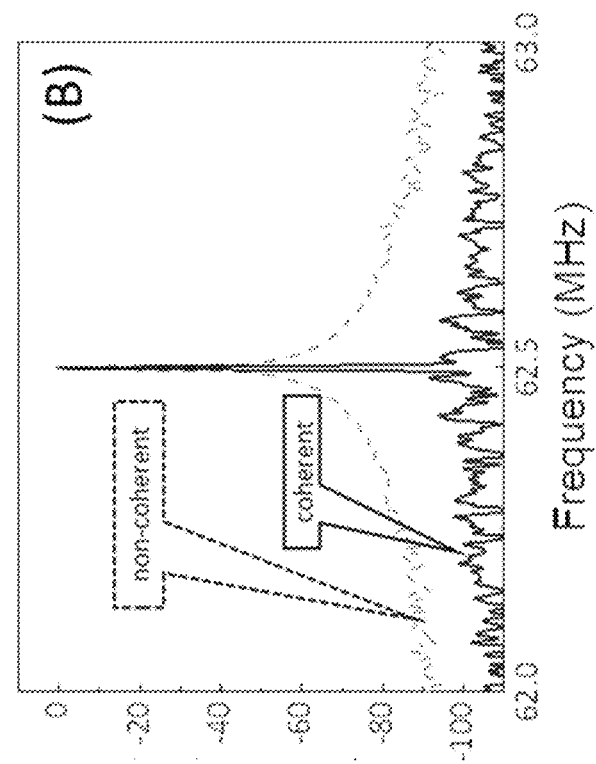
FIG. 3B shows the detail of the comparison of both sampling frequency spectrum from 63 MHz to 63 MHz. The vertical axis of both
Figure 3A:
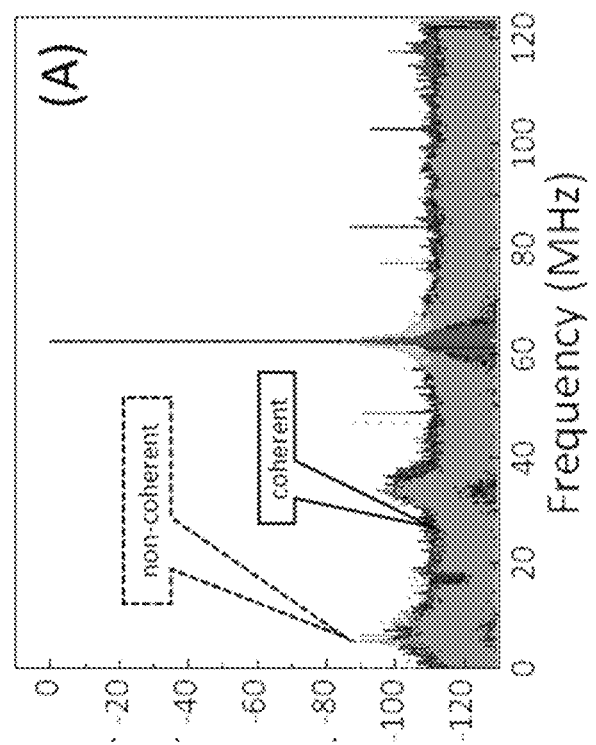
FIG. 3A shows comparison of conventional sampling frequency spectrum with the coherent sampling frequency spectrum in the present invention.
Figure 4:
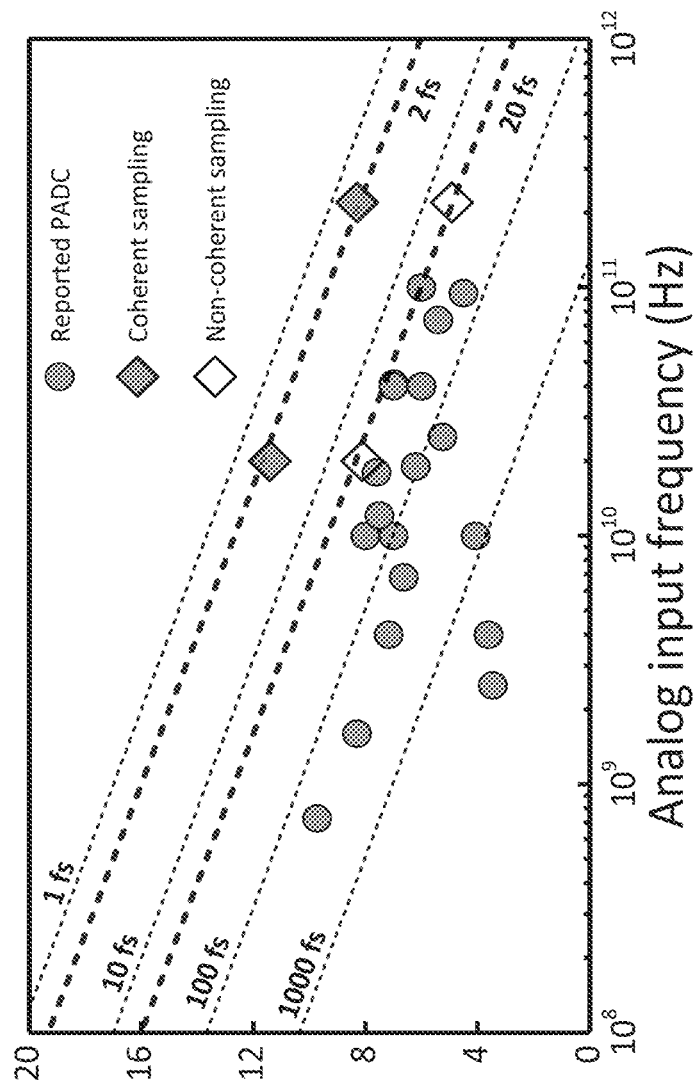
FIG. 4 shows the relation curve between effective bit number and the analog input bandwidth in the present invention, where the vertical axis represents Effective bit number (ENOB).

In the coherent sampling process of the present invention as described above, the photonic sampling gate 3 is used to realize the sampling of optical signal by optical clock and the sampling of electrical signal by optical clock. Referring to FIGS. 2, 3A, 3B, and 4, FIG. 2 shows the result of clock jitter test before and after coherent locking of the system in the present invention, FIG. 3A is a comparison of conventional sampling frequency spectrum with the coherent sampling frequency spectrum in present invention, with FIG. 3B being the detail of the comparison of both sampling frequency spectrum from 63 MHz to 63 MHz, and FIG. 4 shows the relation curve between effective bit number and the analog input bandwidth in present invention.

In addition, in the above process, the phase-locking device locks the sampled optical clock signal source and the source to be taken, thereby achieving phase-parametric sampling, and thereby reducing clock jitter and improving sampling accuracy. It plays a key role in improving the performance of microwave photonic systems that require high time accuracy and high sampling accuracy, such as microwave photonic radar and optical communication systems. The sampling optical clock signal source and the sampled signal source are locked by the phase-locking device to realize coherent sampling, thereby reducing clock jitter and improving sampling precision. It is very important for improving the performance of microwave photon systems that require high time accuracy and high sampling accuracy, such as microwave photon radar and optical communication systems.

We claim:

1. A coherent photon analog-to-digital conversion device, comprising
    an optical clock oscillation source (1) having a first output, a second output, and an input,
    a photon sampling gate (3) having a first input, a second input, and an output,
    a sampled signal source (4) having an output and an input,
    a photoelectric detection module (5) having an input and an output,
    an electrical sampling module (7),
    a phase detection module (9) having a first input, a second input, and an output,
    a loop filter (10) having an input and an output,
    a first signal feedback link (11), and
    a second signal feedback link (12),
    wherein the first output of the optical clock oscillation source (1) is connected with the first input of the photon sampling gate (3);
    the output of the sampled signal source (4) is connected with the second input of the photon sampling gate (3);
    the output of the photon sampling gate (3) is connected with the input of the photoelectric detection module (5);
    the output of the photoelectric detection module (5) is divided into a first part and a second part, the first part is connected with the electrical sampling module (7), and the second part is connected with the first input of the phase detection module (9);
    the second output of the optical clock oscillation source (1) is connected with the second input of the phase detection module (9);
    the output of the phase detection module (9) is connected with the input of the loop filter (10);
    wherein the output of the loop filter (10) is connected with the input of the optical clock oscillation source (1) via the first signal feedback link (11), wherein locking of the optical clock oscillator source (1) is realized; and
    wherein the output of the loop filter (10) is connected with the input of the sampled signal source (4) via the second signal feedback link (12), wherein locking of the sampled signal source (4) is realized.

2. The coherent photon analog-to-digital conversion device of claim 1, wherein the optical clock oscillation source (1) is a passive mode-locked laser, an active mode-locked laser, or a modulation frequency comb.

3. The coherent photon analog-to-digital conversion device of claim 1, wherein the sampled signal source (4) is a voltage controlled oscillator, a frequency synthesizer source, a passive mode-locked laser, an active mode-locked laser, or a modulated frequency comb.

4. The coherent photon analog-to-digital conversion device of claim 1, wherein the photon sampling gate (3) is a lithium niobate electro-optic modulator, a polymer electro-optic modulator, a silicon-based integrated electro-optic modulator, a spatial light modulator, a photonic crystal fiber, or a highly nonlinear fiber.

5. The coherent photon analog-to-digital conversion device of claim 1, wherein the photoelectric detection module is a Positive Intrinsic-Negative or an Avalanche Photo Diode.

6. The coherent photon analog-to-digital conversion device of claim 1, wherein the electrical sampling module (7) is an oscilloscope or an information processing card.

7. The coherent photon analog-to-digital conversion device of claim 1, wherein the phase detection module (10) is a Radio Frequency mixer, which is used for generating a desired mixing signal.

8. The coherent photon analog-to-digital conversion device of claim 1, wherein the loop filter (10) is an Radio Frequency low pass filter.

9. The coherent photon analog-to-digital conversion device of claim 1, wherein the first signal feedback link and the second signal feedback link are power amplifiers or Proportion-Integral-Derivative servers.

* * * * *